United States Patent [19]

Asato

[11] Patent Number: 5,149,832
[45] Date of Patent: * Sep. 22, 1992

[54] MONO AND DIACYL DERIVATIVES OF LL-F28249 COMPOUNDS

[75] Inventor: Goro Asato, Titusville, N.J.

[73] Assignee: American Cyanamid Company, Stamford, Conn.

[*] Notice: The portion of the term of this patent subsequent to Dec. 18, 2007 has been disclaimed.

[21] Appl. No.: 907,281

[22] Filed: Sep. 12, 1986

[51] Int. Cl.$^5$ .............................. C07D 315/00
[52] U.S. Cl. .................................... 549/264
[58] Field of Search ......................... 549/264

[56] References Cited

U.S. PATENT DOCUMENTS

Re. 32,034  11/1985  Chabala et al. ............... 549/264
4,201,861   5/1980   Mrozik et al. ................ 536/7.1

FOREIGN PATENT DOCUMENTS 170006   2/1986  European Pat. Off. .
2166436  5/1986  United Kingdom .

OTHER PUBLICATIONS

H. Mrozik et al, J. Med. Chem. (1982), vol. 25, pp. 658–662.

Primary Examiner—C. Warren Ivy
Attorney, Agent, or Firm—Peggy A. Climenson

[57] ABSTRACT

The present invention relates to novel 5-acyl, 23-acyl and 5,23-diacyl derivtaives of the LL-F28249 compounds. These LL-F28249 compounds (collectively) are isolates from the fermentation broth of *Streptomyces cyaneogriseus* subspecies noncyanogenus having deposit accession number NRRL 15773. The present 5-acyl and 5,23-diacyl compounds are prepared by selective acylation using acid chlorides or anhydrides in the presence of 4-dimethylaminopyridine. The 23-acyl compounds are prepared by selective acylation of the 5-O-silylated LL-F28249 compounds. These novel compounds have potent anthelmintic, insecticidal, ectoparasiticidal, nematicidal and acaricidal activity. Compositions containing these derivatives of LL-F28249 also are described herein.

1 Claim, No Drawings

MONO AND DIACYL DERIVATIVES OF LL-F28249 COMPOUNDS

BACKGROUND OF THE INVENTION

The present invention relates to new 5-acyl, 23-acyl and 5,23-diacyl derivatives of the compounds collectively defined as LL-F28249. These LL-F28249 antibiotics preferably are produced by the fermentation of the microorganism *Streptomyces cyaneogriseus* subspecies *noncyanogenus*, deposited in the NRRL under deposit accession no. 15773. The morphological characteristics, compounds and method for their production is disclosed in European Patent Application Publication No. 170,006, incorporated herein by reference.

The LL-F28249 components are complex macrolides which have hydroxy substituents at the 5, 7 and 23 positions. The selective acylation of the 5- or 23-hydroxy group, or both, affords the 5-acyl, 23-acyl and 5,23-diacyl derivatives of the present invention. The present derivatives of the LL-F28249 compounds are useful for the prevention, treatment or control of helmintic, ectoparasiti insect, acarid and nematode infections and infestations in warm-blooded animals and agricultural crops.

SUMMARY OF THE INVENTION

The present invention provides novel 5-acyl, 23-acyl and 5,23-diacyl derivatives of the compounds designated LL-F28249.

Some of the LL-F28249 compounds have the following structural formula:

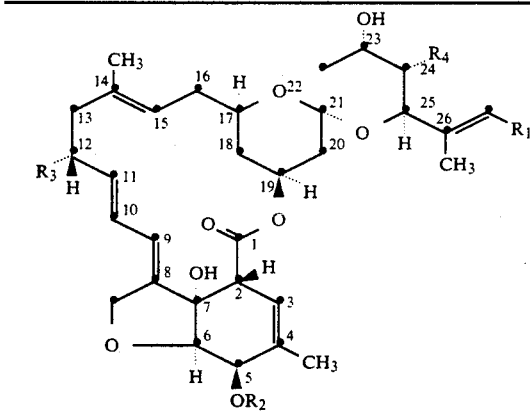

| Component | $R_1$ | $R_2$ | $R_3$ | $R_4$ |
|---|---|---|---|---|
| LL-F28249α | CH(CH$_3$)$_2$ | H | CH$_3$ | CH$_3$ |
| LL-F28249β | CH$_3$ | H | CH$_3$ | CH$_3$ |
| LL-F28249ε | CH(CH$_3$)$_2$ | H | H | CH$_3$ |
| LL-F28249ζ | CH$_2$CH$_3$ | H | CH$_3$ | CH$_3$ |
| LL-F28249Θ | CH(CH$_3$)$_2$ | H | CH$_3$ | CH$_2$CH$_3$ |
| LL-F28249τ | CH(CH$_3$)$_2$ | H | CH$_2$CH$_3$ | CH$_3$ |

The compounds of the present invention are useful anthelmintics, ectoparasiticides, insecticides, acaricides and enmaticides in treating, preventing or controlling such diseases in warm-blooded animals, such as poultry, cattle, sheep, swine, rabbits, horses, dogs, cats and human beings and agricultural crops.

Although these diseases have been recognized for years and therapies exist for the treatment and prevention of the diseases, the present invention provides novel compounds in the search for effective such therapy. For instance, U.S. applications for Letters Patent Ser. No. 907,186, 907,283, 907,188, 907,259, 907,187 and 907,284 of Asato and Asato et al, filed concurrently herewith and incorporated herein by reference thereof provide compounds for such treatments.

U.S. Pat. No. 3,950,360, Aoki et al, Apr. 13, 1976 discloses certain antibiotic substances obtained by culturing a Streptomyces microorganism, said compounds being useful as insecticides and acaricides. Further, an entire series of U.S. patents relates to certain compounds produced by the fermentation of *Streptomyces avermitilis* (U.S. Pat. No. 4,171,314, Chabala et al, Oct. 16, 1979; U.S. Pat. No. 4,199,569, Chabala et al, Apr. 22, 1980; U.S. Pat. No. 4,206,205, Mrozik et al, Jun. 3, 1980; U.S. Pat. No. 4,310,519, Albers-Schonberg, Jan. 12, 1982; U.S. Pat. No. 4,333,925, Buhs et al, Jun. 8, 1982). U.S. Pat. No. 4,423,209, Mrozik, Dec. 27, 1983 relates to the process of converting some of these less desirable components to more preferred ones Finally, British Patent Application No. 2166436 A discloses antibiotics also.

The present compounds or the pharmaceutically and pharmacologically acceptable salts thereof exhibit excellent and effective treatment, prevention and/or control of these serious diseases of warm-blooded animals.

It is an object of the present invention, therefore, to provide novel 5-acyl and 5,23-diacyl derivatives of the LL-F28249 compounds. It is a further object to provide a process for the preparation of these derivatives and to provide methods for preventing, treating or controlling endo and ecto (collectively parasitic), insect, nematode, acarid and helmintic diseases and infestations in warm-blooded animals and agricultural crops by providing compositions containing prophylactically, therapeutically or pharmaceutically-effective amounts of the present novel compounds.

These and other objects of the invention will become apparent by the more detailed description of the invention provided hereinbelow.

DETAILED DESCRIPTION OF THE INVENTION

The LL-F28249 compounds which may act as precursors of the present compounds are represented by the following structural formula,

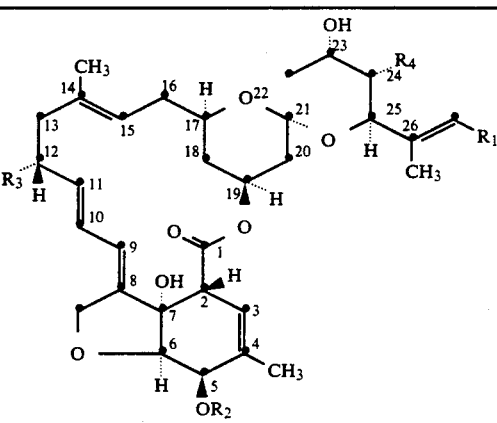

| Component | $R_1$ | $R_2$ | $R_3$ | $R_4$ |
|---|---|---|---|---|
| LL-F28249α | CH(CH$_3$)$_2$ | H | CH$_3$ | CH$_3$ |
| LL-F28249β | CH$_3$ | H | CH$_3$ | CH$_3$ |
| LL-F28249ε | CH(CH$_3$)$_2$ | H | H | CH$_3$ |
| LL-F28249ζ | CH$_2$CH$_3$ | H | CH$_3$ | CH$_3$ |

-continued

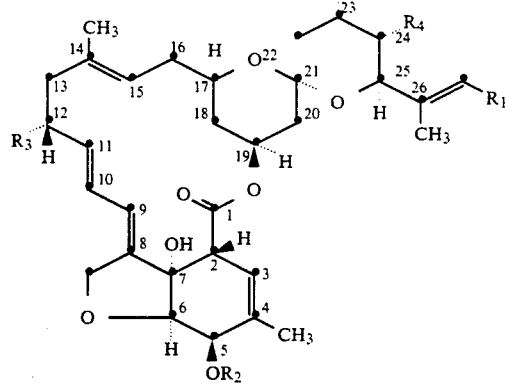

| Component | R₁ | R₂ | R₃ | R₄ |
|---|---|---|---|---|
| LL-F28249θ | CH(CH₃)₂ | H | CH₃ | CH₂CH₃ |
| LL-F28249τ | CH(CH₃)₂ | H | CH₂CH₃ | CH₃ |

The compounds of the instant invention are represented by the following structural formula:

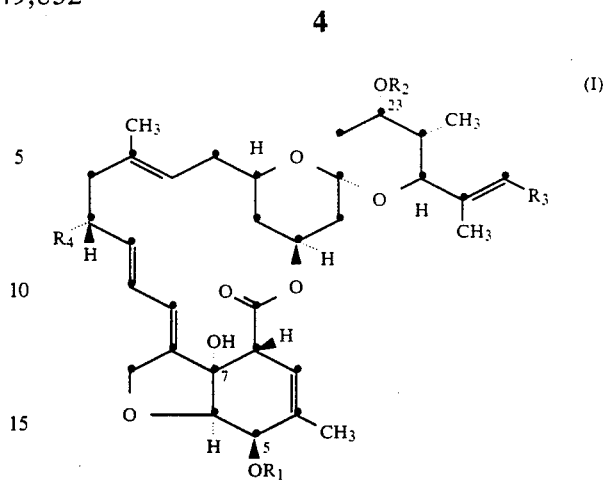

wherein $R_1$ and $R_2$ are each hydrogen, $C_1$–$C_5$ alkanoyl, chloroacetyl, methoxyacetyl, dichloroacetyl, trichloroacetyl, trifluoroacetyl ethylsuccinoyl or carboxypropionyl; $R_3$ is methyl or isopropyl; $R_4$ is hydrogen, methyl or ethyl; with the proviso that both $R_1$ and $R_2$ cannot simultaneously be hydrogen; and the pharmaceutically and the pharmacologically acceptable salts thereof.

A preferred group of compounds of structure (I) include compounds wherein $R_1$ and $R_2$ are each hydrogen, $C_1$–$C_3$ alkanoyl, chloroacetyl, dichloroacetyl, trichloroacetyl, trifluoroacetyl or methoxyacetyl; $R_3$ is isopropyl; $R_4$ is methyl; with the proviso as set forth hereinabove.

The most preferred group of compounds of structure (I) are ones wherein $R_1$ and $R_2$ are each hydrogen, acetyl, chloroacetyl or methoxyacetyl; $R_3$ is isopropyl; $R_4$ is methyl; with the proviso as set forth hereinabove.

The preparation of the 5-acyl and 23-acyl derivatives of the present invention from the corresponding 5-OH and 23-OH LL-F28249 component is schematically indicated hereinbelow. The specific LL-F28249 precursor component exemplified is the alpha component, but it is noted that the appropriate other LL-F28249 components may be substituted therein.

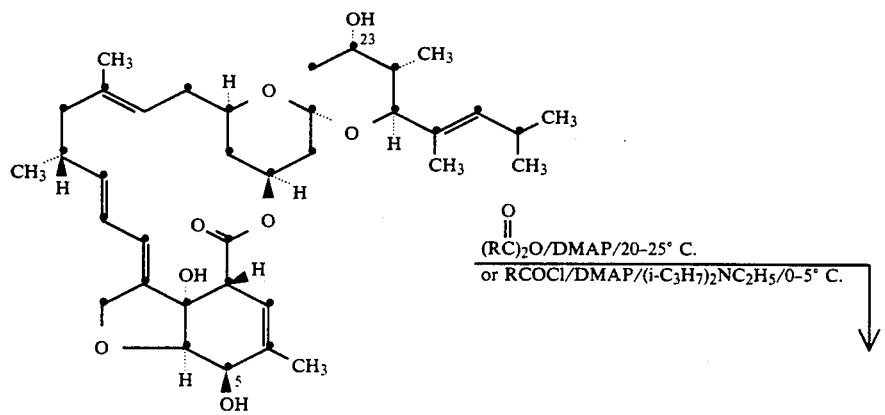

LL-F28249α

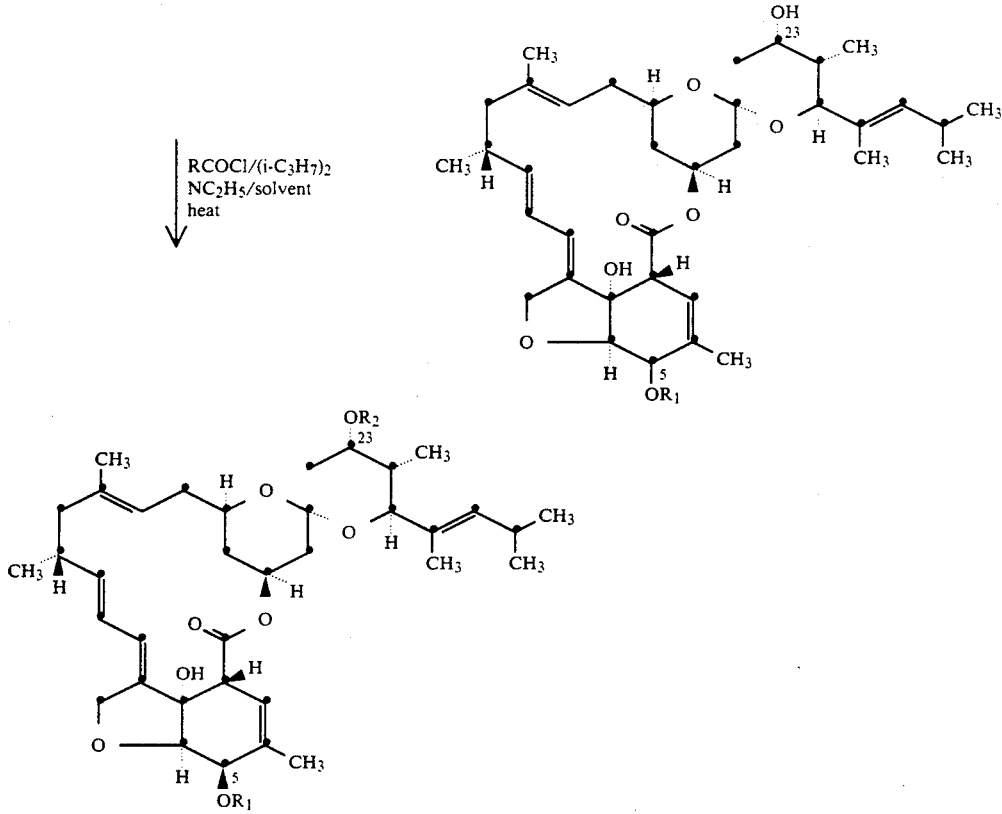

wherein $R_1 = R_2$

The hydroxyl group of the LL-F28249 component is readily acylated with acid chlorides, such as acetyl chloride, chloroacetyl chloride or methoxyacetyl chloride, or acid anhydrides, such as acetic anhydride, succinic anhydride, chloroacetic anhydride or methoxyacetic anhydride, in an aprotic solvent, such as methylene chloride, ethylenedichloride, pyridine, tetrahydrofuran and the like. This acylation is usually conducted in the presence of a catalytic amount of 4-dimethylaminopyridine. When an acid chloride is used an acid acceptor, such as tertiary amines including triethylamine or diisopropylamine, should be used. The reaction temperature is generally maintained near 0° C. but may range between −20° C. to 10° C. to control selectivity, yields and reaction times, as desired.

When acylation of both of the 5-hydroxyl and 23-hydroxyl groups is desired, the reaction is conducted at 50° C. to 100° C. in higher boiling solvents, such as ethylene dichloride or chlorobenzene, to insure acylation of the 23-hydroxyl group. The above-mentioned reagents also are used in the diacylation, but the acid chlorides are preferred as acylating reagents because of their higher reactivity. Tertiary amines, such as triethylamine or diisopropylethylamine, as acid halide acceptors are used with acid halides.

In preparing the compounds of the present invention, other hydroxy groups must be protected. Therefore, prior to the acylation of the 23-hydroxyl group to the 23-acyl group is carried out, the 5-hydroxyl group is protected. Suitable protecting groups are trisubstituted silyl groups, such as t-butyldimethylsilyl and trimethylsilyl, or trisubstituted silyloxyacetyl groups, such as t-butyldimethylsilyloxy acetyl group. The protecting groups, however, are not limited to these groups since other useful protecting groups such as acyl and substituted acyl, such as acetyl, trifluoroacetyl, chloroacetyl, trichloroacetyl, phenoxyacetyl and the like, are also useful in the present process.

One of the preferred protecting groups is t-butyldimethylsilyl. This group is attached to the 5-hydroxyl group by reacting an unprotected 5-hydroxy F-28249 compound with t-butyldimethylsilyl chloride in the presence of a base, such as imidazole, pyridine, 4-dimethylaminopyridine, triethylamine and the like, in an aprotic solvent such as methylene chloride, toluene, ethylacetate, tetrahydrofuran, ethylenedichloride and the like. The reaction is stirred at a temperature of about 0° C. to 30° C., and the reaction is complete in several hours, depending on the temperature of the reaction. The completion of the reaction is usually monitored by high performance liquid chromatography (HPLC) using reverse phase on a Whatman Partisil CCS/C$_8$ rapid analysis column.

Another preferred protecting group is t-butyldimethylsilyloxy acetyl group. This group is attached to the 5-hydroxyl group by combining the unprotected F-28249 compound in an aprotic solvent such as methylene chloride, toluene, ethyl acetate, tetrahydrofuran, ethylenedichloride and the like, containing a tertiary amine, such as pyridine or triethylamine, and adding the protecting agent in the form of an acid halide. The reaction is conducted at a temperature of about 0° C. to 30° C. and is monitored by HPLC for completion.

The silyl protecting group is removed by stirring the protected F28249 compound in a lower alkanol such as methanol at 0° to room temperature for about 0.5 hour to an hour in the presence of an acid such as p-toluenesulfonic acid.

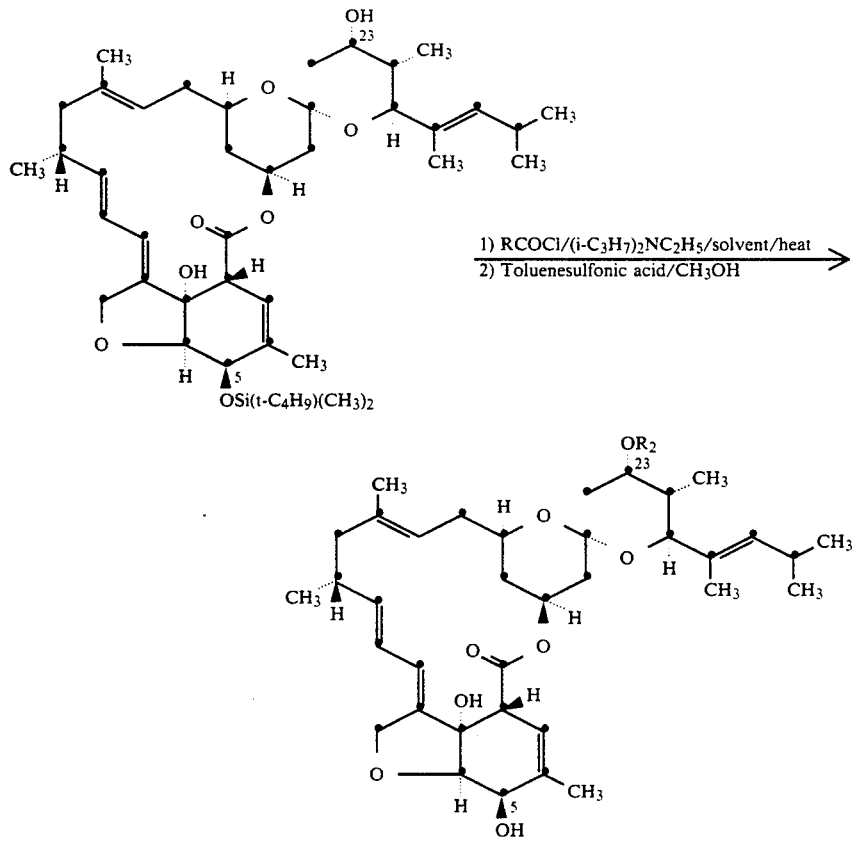

The novel compounds of the present invention have significant activity as anthelmintics, ectoparasiticides, insecticides, nematicides and acaricides in human and animal health areas and in agriculture.

The disease or group of diseases described generally as helminthiasis is due to infection of an animal host with parasitic worms known as helminths. Helminthiasis is a prevalent and serious economic problem in domesticated animals such as swine, sheep, horses, cattle, goats, dogs, cats and poultry. Among the helminths, the group of worms described as nematodes causes widespread and often times serious infection in various species of animals. The most common genera of nematodes infecting the animals referred to above are Haemonchus, Trichostrongylus, Ostertagia, Nematodirus, Cooperia, Ascaris, Bunostomum, Oestophagostomum, Chabertia, Trichuris, Strongylus, Trichonema, Dictyocaulus, Capillaria, Heterakis, Toxocara, Ascaridia, Oxyuris, Ancylostoma, Uncinaria, Toxascaris and Paracaris. Certain of these, such as Nematodirus, Cooperia, and Oesphagostomum primarily attack the intestinal tract while others, such as Haemonchus and Ostertagia, are most prevalent in the stomach. Still others such as Dictyocaulus are found in the lungs. Also, other parasites may be located in other tissues and organs of the body such as the heart and blood vessels, subcutaneous and lymphatic tissue and the like. The parasitic infections known as helminthiases lead to anemia, malnutrition, weakness, weight loss, severe damage to the walls of the intestinal tract and other tissues and organs, and if left untreated, may result in death of the infected host. The present derivatives of the LL-F28249 compounds of this invention unexpectedly have high activity against these parasites. Additionally, they also are active against Dirofilaria in dogs, Nematospiroides, Syphacia, Aspiculuris in rodents, arthropod ectoparasites such as ticks, mites, lice, fleas, blowfly of animals and birds, the ectoparasite Lucilia sp. of sheep, biting insects and migrating dipterous larvae such as Hypoderma sp. in cattle, Gastrophilus in horses and Cuterebra sp. in rodents.

The compounds of the present invention also are useful in treating, preventing or controlling parasites which infect human beings, as well. The most common genera of parasites of the gastrointestinal tract of man are Ancylostoma, Necator, Ascaris, Strongyloides, Trichinella, Capillaria, Trichuris, and Enterobius. Other medically important genera of parasites which are found in the blood or other tissues and organs outside the gastrointestinal tract are the filiarial worms such as Wuchereria, Brugia, Onchocerca and Loa, Dracunculus and extra-intestinal stages of the intestinal worms Strongyloides and Trichinella. The present compounds also are of value against arthropods parasitizing man, biting insects and other dipterous pests causing annoyance to man.

These compounds further are active against household pests such as the cockroach, Blattella sp., clothes moth, Tineola sp., carpet beetle, Attagenus sp., and the housefly Musca domestica.

Insect pests of stored grains such as Tribolium sp., Tenebrio sp., and of agricultural plants such as spider mites (Tetranycus sp.), southern army worms, tobacco budworms, boll weevils, aphids (Acyrthiosiphon sp.), migratory orthopterans such as locusts and immature stages of insects living on plant tissue are controlled by the present compounds as well as the control of soil nematodes and plant parasites such as Meloidogyne sp., which may be of importance in agriculture.

The compounds of the present invention may be administered orally or parenterally for animal and human usage, while they may be formulated in liquid or solid form for agricultural use. Oral administration may take the form of a unit dosage form such as a capsule, bolus or tablet, or as a liquid drench where used as an anthelmintic for animals.

The animal drench is normally a solution, suspension or dispersion of the active compound, usually in water, together with a suspending agent such as bentonite and a wetting agent or like excipient. Generally, the drenches also contain an antifoaming agent. Drench formulations generally contain about 0.001% to 0.5%, by weight, of the active compound. Preferred drench formulations contain about 0.01% to 0.1% by weight.

Capsules and boluses comprise the active ingredient admixed with a carrier vehicle such as starch, talc, magnesium stearate or di-calcium phosphate.

Where it is desired to administer the 5-acyl, 23-acyl or 5,23-diacyl derivatives of LL-F28249 in a dry, solid unit dosage form, capsules, boluses or tablets containing the desired amount of active compound usually are employed. These dosage forms are prepared by intimately and uniformly mixing the active ingredient with suitable finely divided diluents, fillers, disintegrating agents and/or binders such as starch, lactose, talc, magnesium stearate, vegetable gums and the like. Such unit dosage formulations may be varied widely with respect to their total weight and content of the active compound depending upon factors such as the type of host animal to be treated, the severity and type of infection and the weight of the host.

When the active compound is to be administered via an animal feedstuff, it is intimately dispersed in the feed or used as a top dressing or in the form of pellets which may then be added to the finished feed or optionally fed separately. Alternatively, the active compounds of the present invention may be administered to animals parenterally, such as by intraruminal, intramuscular, intratracheal, or subcutaneous injection. In such an event, the active compound is dissolved or dispersed in a liquid carrier vehicle.

For parenteral administration, the active compound is suitable admixed with an acceptable vehicle, preferably of the vegetable oil variety such as peanut oil, cotton seed oil and the like. Other parenteral vehicles such as organic preparations using solketal, propylene glycol, glycerol formal, and aqueous parenteral formulation also are used. The active 5-acyl, 23-acyl or 5,23-diacyl compounds of the present invention are dissolved or suspended in the parenteral formulation for administration. Such formulations generally contain about 0.005% to 5%, by weight, of the active compound.

Although the compounds of the present invention are primarily used in the treatment, prevention or control of helminthiasis, they also are useful in the prevention and treatment of diseases caused by other parasites. For example, arthropod parasites such as ticks, lice, fleas, mites and other biting insects in domesticated animals and poultry are controlled by the present compounds. These compounds also are effective in treatment of parasitic diseases that occur in other animals including human beings. The optimum amount to be employed will, of course, depend upon the particular compound employed, the species of animal to be treated and the type and severity of parasitic infection or infestation.

Generally, the amount useful in oral administration of these novel compounds is about 0.001 mg to 10 mg per kg of animal body weight, such total dose being given at one time or in divided doses over a relatively short period of time (1-5 days). The preferred compounds of the invention give excellent control of such parasites in animals by administering about 0.025 mg to 3 mg per kg of animal body weight in a single dose. Repeat treatments are given as required to combat re-infections and are dependent upon the species of parasite and the husbandry techniques being employed. The techniques for administering these materials to animals are known to those skilled in the veterinary field.

When the compounds described herein are administered as a component of the animal's feed, or dissolved or suspended in the drinking water, compositions are provided in which the active compound or compounds are intimately dispersed in an inert carrier or diluent. An inert carrier is one that will not react with the active component and that will be administered safely to animals. Preferably, a carrier for feed administration is one that is, or may be, an ingredient of the animal ration.

Suitable compositions include feed premixes or supplements in which the active compound is present in relatively large amounts, wherein said feed premixes or supplements are suitable for direct feeding to the animal or for addition to the feed either directly or after an intermediate dilution or blending step.

Typical carriers or diluents suitable for such compositions include distillers' dried grains, corn meal, citrus meal, fermentation residues, ground oyster shells, wheat shorts, molasses solubles, corn cob meal, edible bean mill feed, soya grints, crushed limestone and the like. The active compounds are intimately dispersed throughout the carrier by methods such as grinding, stirring, milling or tumbling. Compositions containing about 0.005% to 2.0%, by weight, of the active compound are particularly suitable as feed premixes.

Feed supplements, which are fed directly to the animal, contain about 0.0002% to 0.3%, by weight, of the active compounds. Such supplements are added to the animal feed in an amount to give the finished feed the concentration of active compound desired for the treatment, prevention and/or control of parasitic diseases. Although the desired concentration of active compound will vary depending upon the factors previously mentioned as well as upon the particular derivative employed, the compounds of this invention are usually fed at concentrations of about 0.00001% to 0.02% in the feed in order to achieve the desired antiparasitic result.

The compounds also may be administered by pouring on the skin of animals via a solution. Generally, the active compounds are dissolved in a suitable inert solvent, such as dimethylsulfoxide, propylene glycol of the like, alternatively in combination of solvents, for the pour-on administration.

The compounds of this invention also are useful in combating agricultural pests that inflict damage upon growing or stored crops. The present compounds are applied, using known techniques such as sprays, dusts, emulsions and the like, to the growing or stored crops to effect protection from such agricultural pests.

The present invention is illustrated by the following examples which are illustrative of said invention and not limitative thereof.

EXAMPLE 1

5-O-t-Butyldimethylsilyl-LL-F28249α

In 500 mL of $CH_2Cl_2$, 70 g of LL-F28249α is stirred with 82.04 g of imidazole at 20° C. under $N_2$ atmosphere, and 43 g of t-butyldimethylsilyl chloride in 400 mL of $CH_2Cl_2$ is added over 5 minutes. After an hour, the reaction is assayed for completion by high performance liquid chromatography (HPLC), using 50% $CH_3CN$/50% $H_2O$ in a curved gradient mode over 10 minutes on a Whatman $C_8$-RAC column at 1 mL/min. Another 3 g of t-butyldimethylsilyl chloride is added, and after 3 hours, the composition is 92.3% product, 0.3% LL-F28249α and 1.16% disilylated material. The mixture is diluted with $CH_2Cl_2$ and poured into 2 L of $H_2O$, and the $CH_2Cl_2$ layer is separated. The aqueous portion is extracted with 2 L of $CH_2Cl_2$, and the combined organic layers are dried ($Na_2SO_4$). The $CH_2Cl_2$ is evaporated in vacuo to afford 116 g of the title compound that is identified by mass spectrometry and nuclear magnetic resonance (NMR) spectrometry.

EXAMPLE 2

5-Methoxyacetoxy-LL-F28249α

In 6mL of $CH_2Cl_2$ containing 50.34 mg of LL-28249α, 40 mg of 4-dimethylaminopyridine and 44 mg of diisopropylethylamine are added. The mixture is stirred under $N_2$ atmosphere in an ice bath, and 30 mg of methoxyacetyl chloride is added. After stirring 2 hours, the mixture is poured into ice-$H_2O$, and the admixture is made acidic with 1:1 aq. HCl and extracted with $3 \times 10$ mL of $CH_2Cl_2$. The $CH_2Cl_2$ extracts are dried and ($Na_2SO_4$) evaporated to dryness to afford the crude product, which is purified on a silica gel preparative chromatography plate using 5:1 $CH_2Cl_2$/EtOH. The title product is extracted from silica gel with 20% MeOH in $CH_2Cl_2$ and identified by mass spectrometry and NMR spectroscopy.

EXAMPLE 3

5,23-Bis(methoxyacetoxy-LL-F28249α

In 5 mL of 1,2-ethylenedichloride, 84 mg of LL F28249α is dissolved, and 74 mg of diisopropylethylamine and 11.9 mg of methoxyacetyl chloride are added. The mixture is heated at reflux temperature under $N_2$ atmosphere for 20 hours and poured into ice-$H_2O$. The aqueous mixture is extracted with $3 \times 10$ mL of $CH_2Cl_2$, and the combined extracts are washed with $H_2O$ and dried ($Na_2SO_4$). After removal of the solvent by evaporation, the crude product is purified by chromatography as in Example 2. The title product is identified by mass spectrometry and NMR spectroscopy

EXAMPLE 4

23-Acetoxy-LL-F28249α

In 1 Ml of dry pyridine, 51.75 mg of 5-t-butyldimethylsilyloxy-LL-F28249α, 5 drops of $Ac_2O$ and a few crystals of 4-methylaminopyridine are heated under $N_2$ in an oil bath at 75° C. for 7 hours. The mixture is poured into ice-$H_2O$ and extracted with $2 \times 25$ mL of $CH_2Cl_2$. The combined extracts are washed with $H_2O$ and evaporated to dryness. The residue is dissolved in 9 mL of MeOH containing 72 mg of p-toluenesulfonic acid and stirred for 1 hour. The MeOH is evaporated and the residue is dissolved in 30 mL of EtOAc and washed with dilute $NaHCO_3$ solution and $H_2O$. The solution is dried ($MgSO_4$) and evaporated to dryness. The residue is purified by chromatography as in Example 2, and the title compound is identified by mass spectrometry and NMR spectroscopy.

EXAMPLE 5

5-Acetoxy-LL-F28249α

In 0.75 mL of dry pyridine, 50 mg of LL-F28249α, 2 drops of $Ac_2O$ and a few crystals of 4-dimethylaminopyridine are stirred at room temperature for 2 hours and poured into ice-$H_2O$. The mixture is acidified and extracted with $3 \times 2$ mL of $CH_2Cl_2$. The extracts are dried ($MgSO_4$), evaporated to dryness and purified on silica gel preparative chromatography plates using 20 $CH_2Cl_2$/1 EtOAc. The title product is extracted from silica gel with 10% MeOH in $CH_2Cl_2$ and identified by mass spectrometry and NMR spectroscopy.

EXAMPLE 6

5-Carboxypropionyloxy-LL-F28249α

In the manner described in Example 5, LL-F28249α is reacted with succinic anhydride to afford the title compound that is identified by mass spectrometry and NMR spectroscopy.

EXAMPLE 7

5-Chloroacetyl-LL-F28249α

Using the method of Example 2, LL-F28249α is reacted with $ClCH_2COCl$ at 0° C. to afford the title compound that is identified by mass spectrometry and NMR spectroscopy.

EXAMPLES 8–14

5-Acyloxy-LL-F28249α

Using the method of Example 2, the following 5-acyloxy-LL-F28249α compounds are prepared using the appropriate acid chloride: 5-trifluoroacetoxy-, dichloroacetoxy-, trichloroacetoxy-, propionyoxy-, ethylsuccinoyloxyhexanoyloxy and pivaloyoxy LL-F28249α.

EXAMPLES 15–18

5,23-Bis(acyloxy)-LL-F28249α

Using the method of Example 3, the following bis-acylated LL-F28249α compounds are prepared: 5,23-bis(acetoxy)-, 5,23-bis(trichloroacetoxy)-, 5,23-propionyloxy- and ethylsuccinoyloxy-LL-F28249α.

EXAMPLES 19–21

23-Acyloxy-LL-F28249α

Using the method of Example 3, 5-t-butyldimethylsilyloxy-LL-F28249α is acylated at the 23-OH position with the appropriate acyl halides and deprotected by the method of Example 4 to afford the following 23-acyloxy-LL-F28249α compounds: 23-chloroacetoxy-, 23-ethylsuccinoyloxy- and 23-propionyloxy-LL-F28249α.

EXAMPLES 22–24

Using the procedure of Example 4, the following 23-acetyl compounds are prepared:

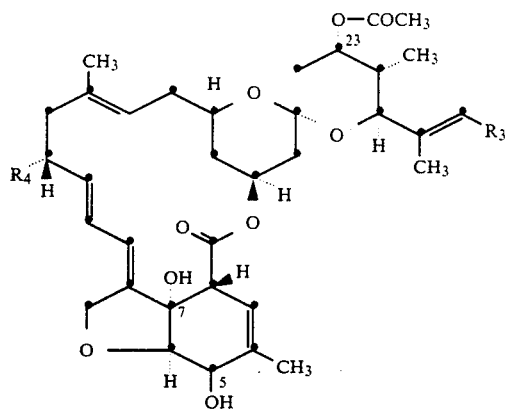

| $R_3$ | $R_4$ |
|---|---|
| i-C$_3$H$_7$ | H |
| C$_2$H$_5$ | CH$_3$ |
| i-C$_3$H$_7$ | C$_2$H$_5$ |

EXAMPLES 25-27

Using the procedure of Example 3, the following 5,23-bis(methoxyacetyl) compounds are prepared:

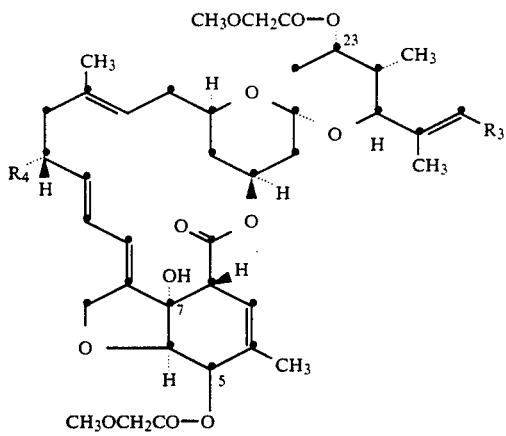

| $R_3$ | $R_4$ |
|---|---|
| i-C$_3$H$_7$ | H |
| C$_2$H$_5$ | CH$_3$ |
| i-C$_3$H$_7$ | C$_2$H$_5$ |

EXAMPLES 28-30

Using the procedure of Example 5, the following 5-acetyl compounds are prepared:

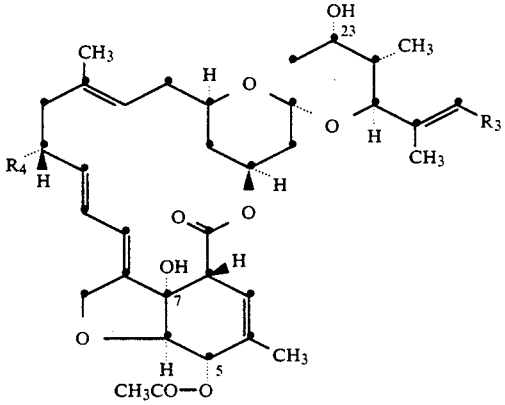

| $R_3$ | $R_4$ |
|---|---|
| i-C$_3$H$_7$ | H |
| C$_2$H$_5$ | CH$_3$ |
| i-C$_3$H$_7$ | C$_2$H$_5$ |

What is claimed is:

1. A compound represented by structural formula (I):

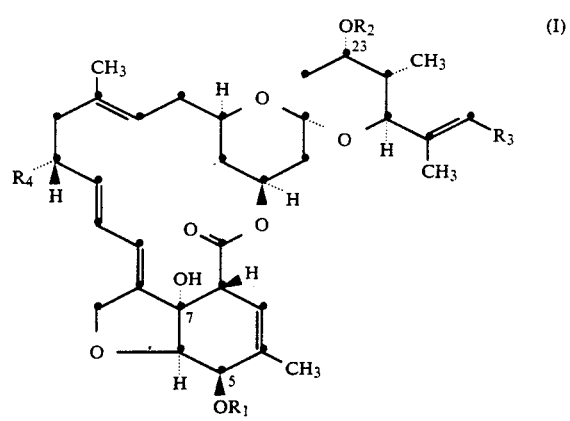

wherein $R_1$ is acetyl; $R_2$ is hydrogen; $R_3$ is isopropyl; and $R_4$ is methyl.

* * * * *

UNITED STATES PATENT OFFICE
CERTIFICATE OF CORRECTION

Patent No. 5,149,832        Dated September 22, 1992

Inventor(s) Asato et al.        Page 1 of 13

It is certified that error appears in the above-identified patent and that said Letters Patent is hereby corrected as shown below:

In the Abstract, line 2, should read "derivatives" instead of ..derivtaives..;

Column 1, line 23, should read "ectoparasitic" instead of ..ectoparasiti..;

Replace the formula at column 1, lines 35-50, with the following formula:

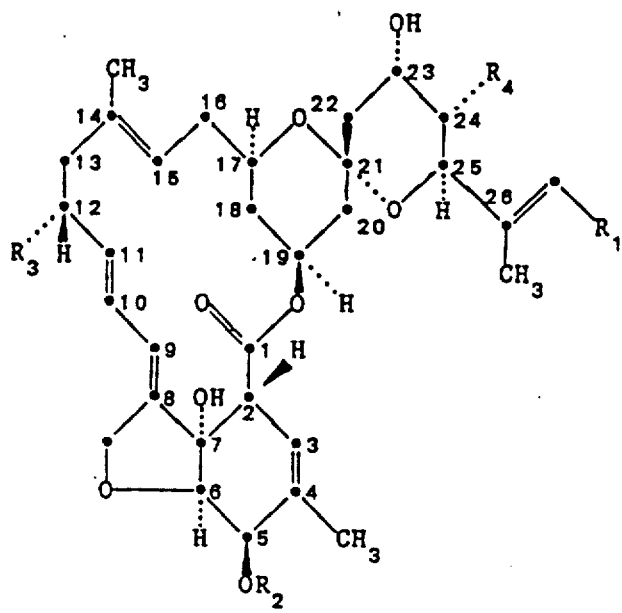

UNITED STATES PATENT OFFICE
CERTIFICATE OF CORRECTION

Patent No. __5,149,832__                    Dated __September 22, 1992__

Inventor(s) __Asato et al.__                       __Page 2 of 13__

It is certified that error appears in the above-identified patent and that said Letters Patent is hereby corrected as shown below:

Column 1, line 60, should read "nematicides" instead of ..enmaticides..;

Replace the formula at column 2 lines 47-63, with the following formula:

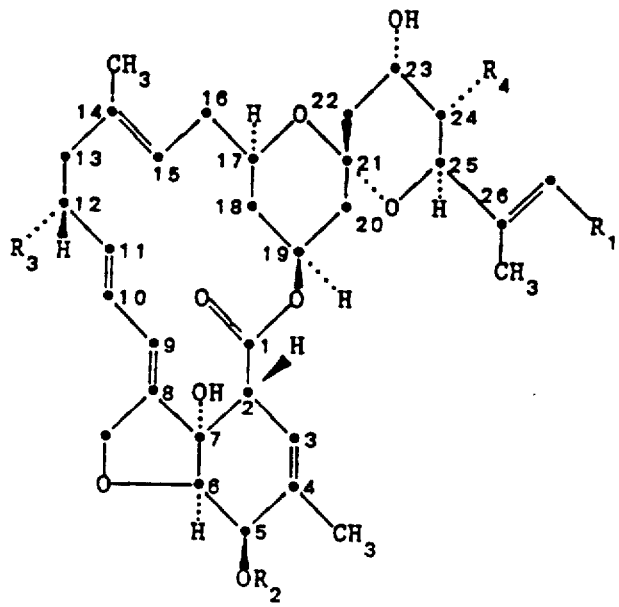

UNITED STATES PATENT OFFICE
CERTIFICATE OF CORRECTION

Patent No. 5,149,832  Dated September 22, 1992

Inventor(s) Asato et al.  Page 3 of 13

It is certified that error appears in the above-identified patent and that said Letters Patent is hereby corrected as shown below:

Replace the formula at column 3, lines 1-18, with the following formula:

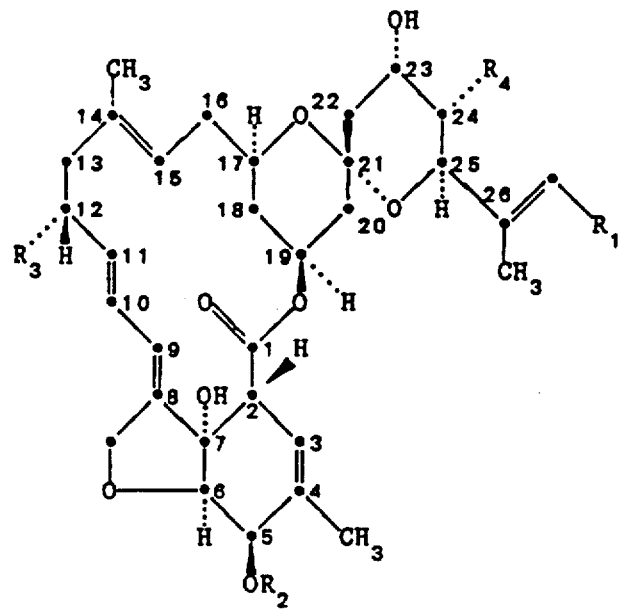

UNITED STATES PATENT OFFICE
CERTIFICATE OF CORRECTION

Patent No. __5,149,832__      Dated __September 22, 1992__

Inventor(s) __Asato et al.__      __Page 4 of 13__

It is certified that error appears in the above-identified patent and that said Letters Patent is hereby corrected as shown below:

Replace formula (I) at column 4, lines 1-18, with the following formula:

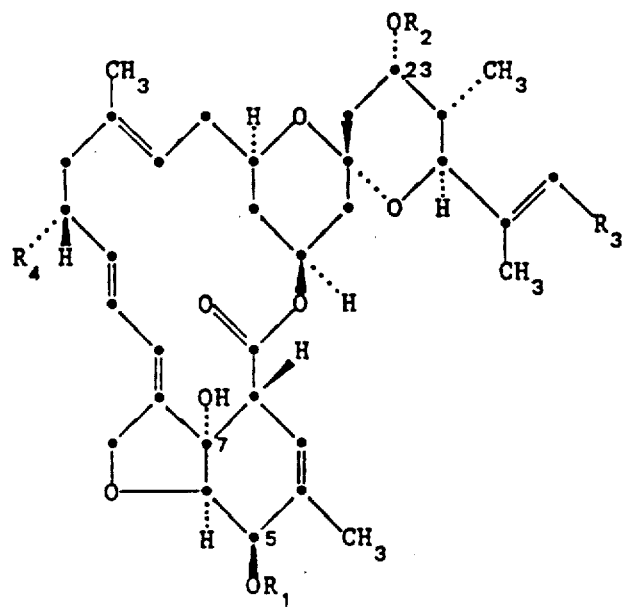

(I)

UNITED STATES PATENT OFFICE
CERTIFICATE OF CORRECTION

Patent No. 5,149,832  Dated September 22, 1992

Inventor(s) Asato et al.  Page 5 of 13

It is certified that error appears in the above-identified patent and that said Letters Patent is hereby corrected as shown below:

Replace the formula at column 3, lines 50-65, with the following formula:

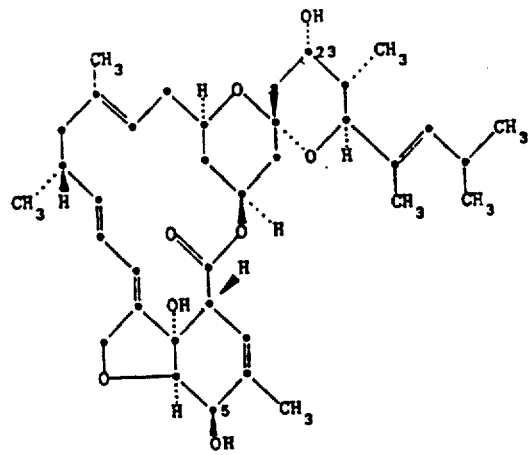

UNITED STATES PATENT OFFICE
CERTIFICATE OF CORRECTION

Patent No. 5,149,832      Dated September 22, 1992

Inventor(s) Asato et al.      Page 6 of 13

It is certified that error appears in the above-identified patent and that said Letters Patent is hereby corrected as shown below:

Replace the formula at column 5, lines 24-34, with the following formula:

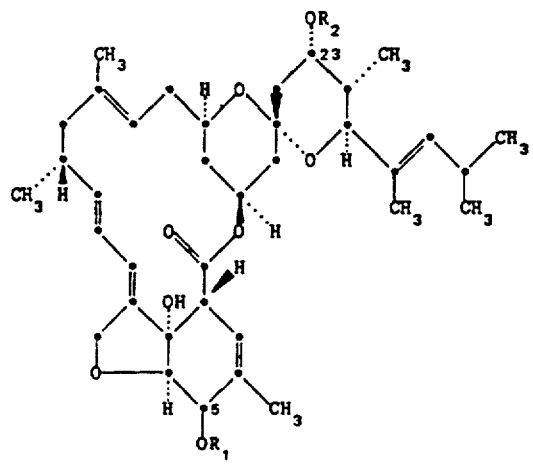

wherein $R_1 = R_2$

UNITED STATES PATENT OFFICE
CERTIFICATE OF CORRECTION

Patent No. 5,149,832          Dated  September 22, 1992

Inventor(s) Asato et al.                    Page 7 of 13

It is certified that error appears in the above-identified patent and that said Letters Patent is hereby corrected as shown below:

Replace the formula at column 6, lines 1-20, with the following formula:

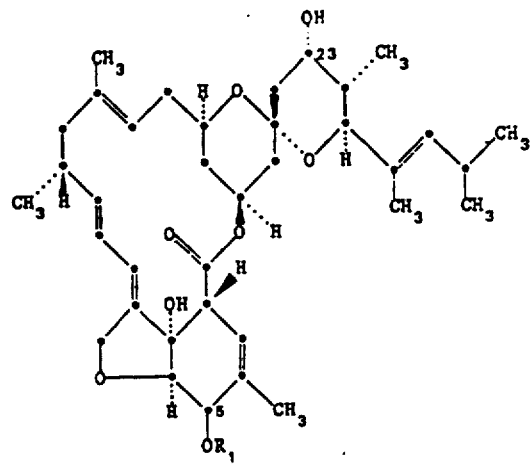

UNITED STATES PATENT OFFICE
CERTIFICATE OF CORRECTION

Patent No. __5,149,832__     Dated __September 22, 1992__

Inventor(s) __Asato et al.__     __Page 8 of 13__

It is certified that error appears in the above-identified patent and that said Letters Patent is hereby corrected as shown below:

Replace the formula at column 7, lines 1-20, with the following formula:

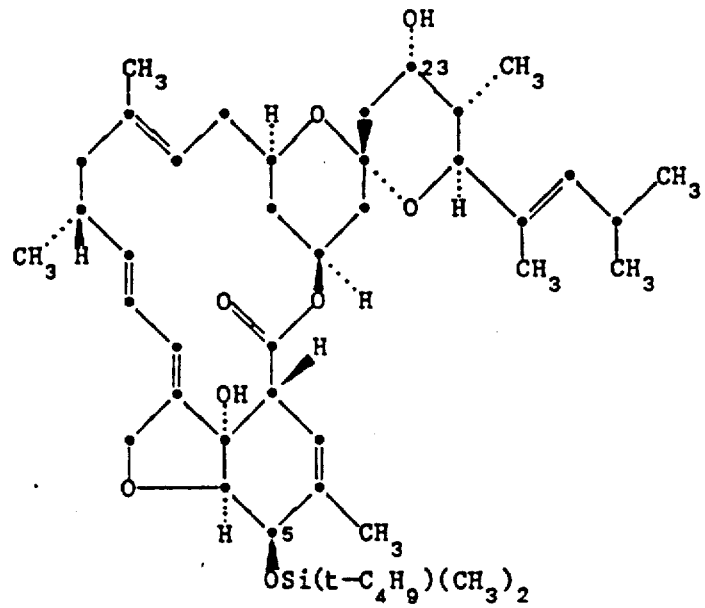

UNITED STATES PATENT OFFICE
CERTIFICATE OF CORRECTION

Patent No. 5,149,832  Dated September 22, 1992

Inventor(s) Asato et al.  Page 9 of 13

It is certified that error appears in the above-identified patent and that said Letters Patent is hereby corrected as shown below:

Replace the formula centered between columns 7 and 8 at lines 24-34, with the following formula:

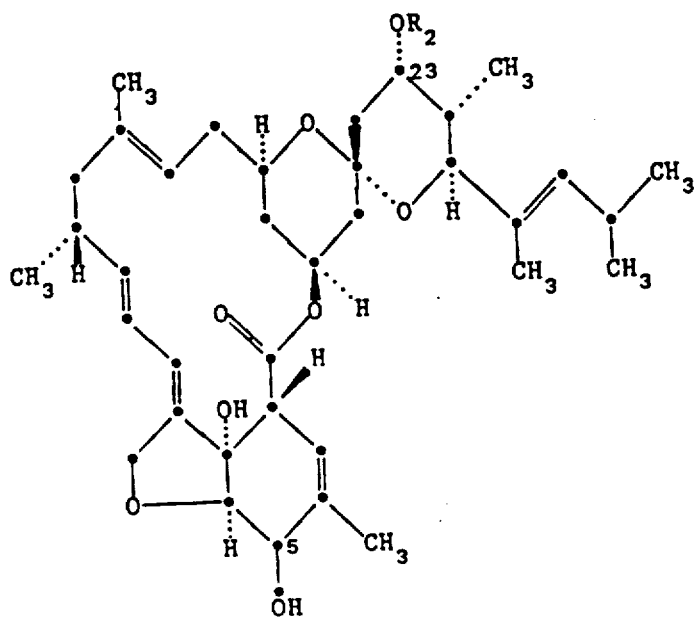

UNITED STATES PATENT OFFICE
CERTIFICATE OF CORRECTION

Patent No. 5,149,832　　　　　　　　　Dated September 22, 1992

Inventor(s) Asato et al.　　　　　　　　Page 10 of 13

It is certified that error appears in the above-identified patent and that said Letters Patent is hereby corrected as shown below:

Replace the formula at column 13, lines 1-19, with the following formula:

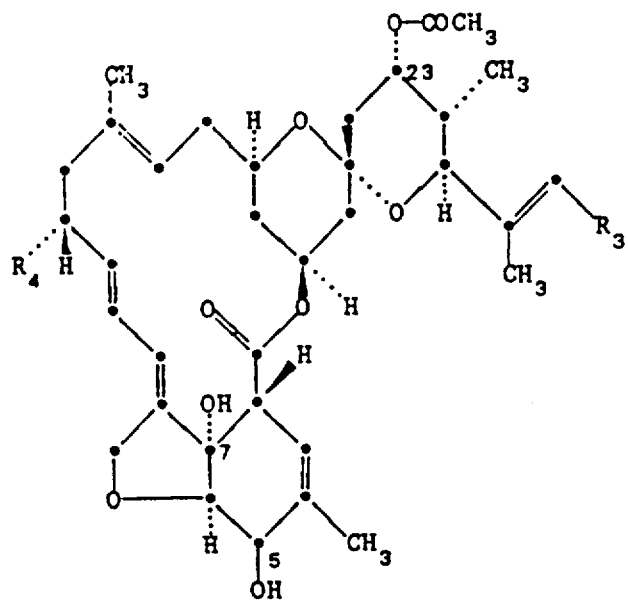

UNITED STATES PATENT OFFICE
CERTIFICATE OF CORRECTION

Patent No. 5,149,832    Dated September 22, 1992

Inventor(s) Asato et al.    Page 11 of 13

It is certified that error appears in the above-identified patent and that said Letters Patent is hereby corrected as shown below:

Replace the formula at column 13, lines 35-50 with the following formula:

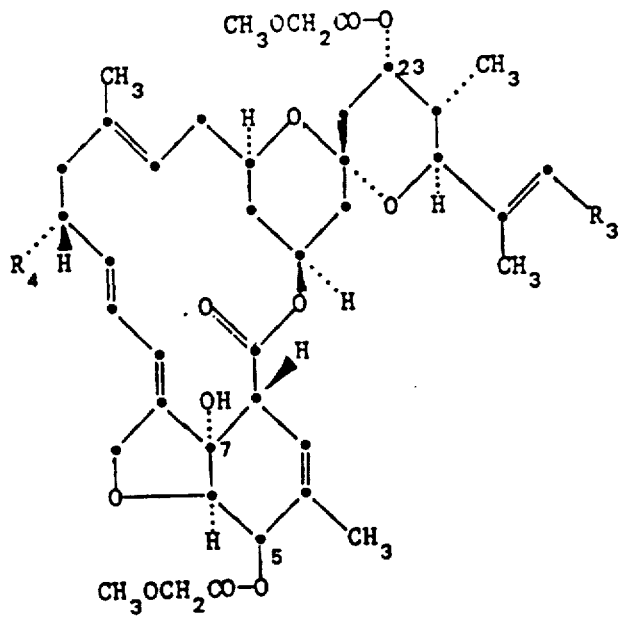

UNITED STATES PATENT OFFICE
CERTIFICATE OF CORRECTION

Patent No. 5,149,832　　　　　　　Dated September 22, 1992

Inventor(s) Asato et al.

It is certified that error appears in the above-identified patent and that said Letters Patent is hereby corrected as shown below:

Replace the formula at column 14 lines 10-25, with the following formula:

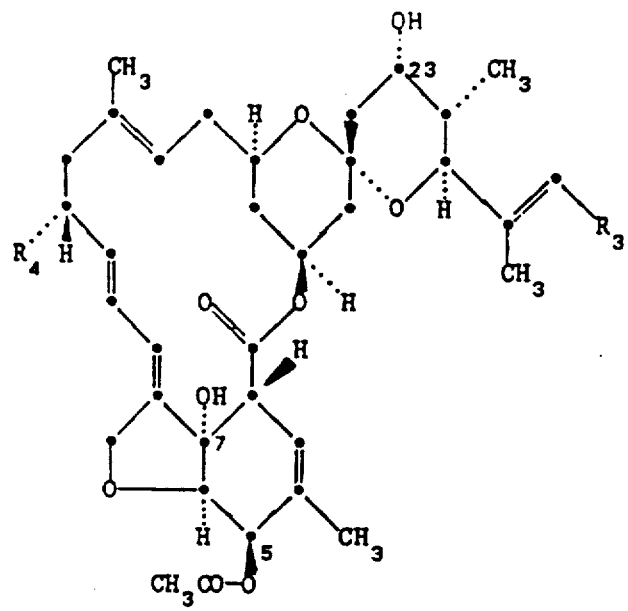

UNITED STATES PATENT AND TRADEMARK OFFICE
CERTIFICATE OF CORRECTION

PATENT NO. : 5,149,832
DATED : September 22, 1992
INVENTOR(S) : Asato et al.

It is certified that error appears in the above-indentified patent and that said Letters Patent is hereby corrected as shown below:

Replace the formula at column 14, lines 35-50, with the following formula:

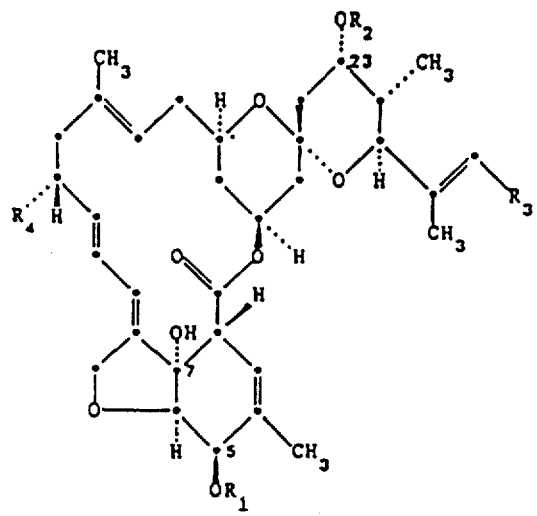

Signed and Sealed this

Twenty-ninth Day of March, 1994

*Attest:*

BRUCE LEHMAN

*Attesting Officer*  Commissioner of Patents and Trademarks